(12) United States Patent
Westphal et al.

(10) Patent No.: US 11,529,172 B1
(45) Date of Patent: Dec. 20, 2022

(54) FERTILITY KITS WITH SYRINGES AND COLLECTION JARS, AND METHOD OF USE

(71) Applicant: PherDal, Dixon, IL (US)

(72) Inventors: Jennifer Westphal, Dixon, IL (US); Ryan Westphal, Dixon, IL (US)

(73) Assignee: PherDal, Dixon, IL (US)

( * ) Notice: Subject to any disclaimer, the term of this patent is extended or adjusted under 35 U.S.C. 154(b) by 0 days.

(21) Appl. No.: 17/526,705

(22) Filed: Nov. 15, 2021

(51) Int. Cl.
*A61B 17/43* (2006.01)
*A61B 10/00* (2006.01)
(Continued)

(52) U.S. Cl.
CPC .......... *A61B 17/43* (2013.01); *A61B 10/0012* (2013.01); *A61B 10/0058* (2013.01);
(Continued)

(58) Field of Classification Search
CPC ....... A61B 17/42; A61B 17/425; A61B 17/43; A61B 10/0096; A61B 10/0058; A61B 10/0012; A61M 5/002; A61M 5/3129; A61M 5/3134; A61M 5/3137; A61M 5/31511; A61M 5/31513; A61M 2005/3131; A61M 2005/31516; A61M 5/315; A61M 2005/31506; A61M 2005/31518; A61M 5/3135; A61M 2005/3139; A61M 5/31505; Y10S 604/906; A61D 19/00–19/027; A61D 19/02; A61D 9/021; A61D 19/022; A61D 19/024; A61D 19/04; C12N 5/061; A61F 5/453; A61F 6/18
See application file for complete search history.

(56) References Cited

U.S. PATENT DOCUMENTS 1,589,046 A * 6/1926 Brix ..................... A61M 5/3135
604/227
3,672,369 A * 6/1972 Brown ............... A61M 5/31511
604/222

(Continued)

OTHER PUBLICATIONS

Mosie Baby, The Mosie Kit, <https://mosiebaby.com/products/the-mosie-kit> (Year: 2021).*

(Continued)

*Primary Examiner* — Bhisma Mehta
*Assistant Examiner* — Hong-Van N Trinh

(57) ABSTRACT

A fertility kit for performing self-insemination, comprising a package with three sets of sterilized disposable syringes and collection jars. Each fertility syringe comprises: an outer rigid tubular barrel and an inner plunger. The barrel comprises a curved distal end with a small circular distal opening, and a sealed proximal end, and an inner hollow tube housing the plunger. The barrel's proximal end also comprises two opposing circular members to fit a user's fingers; and a plunger flat end fitting in-between. The plunger distal end has a has a funnel-like shape that fits into the barrel curved end to push all the semen out while preventing a backflow. The collection jar comprises a sealable lid, and an inner surface comprising smooth seamless edges. Fresh or frozen, unwashed semen is deposited into the jar, pulled into the syringe, and administered cervically during a user's maximum monthly level of luteinizing hormone.

14 Claims, 7 Drawing Sheets

(51) Int. Cl.
*A61M 5/00* (2006.01)
*A61M 5/31* (2006.01)
*A61M 5/315* (2006.01)

(52) U.S. Cl.
CPC ......... *A61B 10/0096* (2013.01); *A61M 5/002* (2013.01); *A61M 5/3134* (2013.01); *A61M 5/3137* (2013.01); *A61M 5/31513* (2013.01)

(56) References Cited

U.S. PATENT DOCUMENTS

| | | | | |
|---|---|---|---|---|
| 4,925,449 | A * | 5/1990 | Saez | A61M 5/007 |
| | | | | 222/386 |
| 7,597,683 | B2 | 10/2009 | Myhrberg | |
| D657,867 | S | 4/2012 | Effenberger | |
| D669,679 | S | 10/2012 | Goldstein | |
| 9,125,688 | B2 | 9/2015 | Fowler | |
| D834,182 | S | 11/2018 | Reynolds et al. | |
| D913,488 | S | 3/2021 | Ransome et al. | |
| 2011/0224482 | A1* | 9/2011 | McCarthy | A61H 19/50 |
| | | | | 600/35 |
| 2014/0013718 | A1* | 1/2014 | Maasarani | B65D 75/326 |
| | | | | 53/492 |
| 2015/0057608 | A1* | 2/2015 | Hitscherich, Jr. | A61M 5/3137 |
| | | | | 604/218 |
| 2015/0320444 | A1* | 11/2015 | Brown | A61B 17/43 |
| | | | | 600/35 |
| 2018/0140409 | A1* | 5/2018 | Jun | A61D 19/021 |
| 2021/0307784 | A1* | 10/2021 | Brown | A61D 19/027 |

OTHER PUBLICATIONS

Mosie Baby, Mosie Baby Bundle, <https://mosiebaby.com/products/mosie-baby-bundle> (Year: 2021).*

Gurevich, R. What is Intrauterine Insemination, published Nov. 11, 2020 on website VeryWellFamily.

Kop, P. A., Mochtar, M. H., et al. (2018). "Intrauterine insemination versus intracervical insemination in donor sperm treatment." The Cochrane database of systematic reviews, 1(1), CD000317.

Kop, PAL, et al. (2015) "Intrauterine insemination or intracervical insemination with cryopreserved donor sperm in the natural cycle: a cohort study", Human Reproduction, 30(3)).

Xu et al., (2020) "Fertility factors affect the vaginal microbiome in women of reproductive age" American J of Reproductive Immunology, 83(4)).

Mosie Baby ICU collection kits, website downloaded on Oct. 17, 2022. https://mosiebaby.com/pages/home?gclid=EAIaIQobChMIhO6kgP_R8wIVrG1vBB2ePg4AEAAYASAAEgleKPD_BwE.

Garcia-Velasco, J, et al. (2020) "The reproductive microbiome—clinical practice recommendations for fertility specialists", RBMO, 41(3): 443-453.

Garcia-Velasco, J, et al. (2017) "What fertility specialists should know about the vaginal microbiome: a review", RBM online, p. 103-112.

Gupta, S, et al. (2019) "Crosstalk between Vaginal Microbiome and Female Health: A review", Microbial Pathogenesis,136(103696): 1-10.

Design U.S. Appl. No. 29/815,536 by Westphal et al., filed Nov. 15, 2021, entitled: "Fertility Syringe".

* cited by examiner

FERTILITY KITS WITH SYRINGES AND COLLECTION JARS, AND METHOD OF USE

FIELD OF THE INVENTION

The present invention relates generally to sets comprising fertility syringes and sperm collection jars for use in at-home intracervical insemination (ICI), applicator kits, and methods of use.

BACKGROUND OF THE INVENTION

Intrauterine Insemination (IUI) requires delivery of washed sperm via a syringe through the cervix and directly into the vagina; while Intracervical Insemination (ICI) requires delivery of unwashed sperm only to the cervical opening. Methods and instruments for conducting IUI and ICI fertility treatments are well known in the art. IUI requires treatments within a clinical setting, to include taking oral and/or injectable fertility drugs, and the washing of sperm. Treatment costs on average about $895; but it can run up to $4000 depending on the clinic (Gurevich, R. *What is Intrauterine Insemination*, published Nov. 11, 2020 on website VeryWellFamily).

A 2018 study showed that during non-medically induced ovulation, Intrauterine Insemination (IUI) and Intracervical Insemination (ICI) have the same live birth rate (Kop, P. A., Mochtar, M. H., et al. (2018). "Intrauterine insemination versus intracervical insemination in donor sperm treatment" *The Cochrane database of systematic reviews*, 1(1)).

ICI is a much less expensive treatment (e.g., the cost of the kit shipped to a user's home). The additional preparation of washing sperm, along with needing to be inside of a clinical setting, results in IUI being approximately 4 times the cost of IUI. Due to the high difference in cost, as well as the unsignificant difference in live birth rate, it's been suggested that over the initial three months, ICI should be the preferred initial treatment (Kop, P A L, et al. (2015) "Intrauterine insemination or intracervical insemination with cryopreserved donor sperm in the natural cycle: a cohort study", *Human Reproduction*, 30(3)).

Fertility syringes for both IUI and ICI methods are well known in the art; but most available syringes are generally intended for use within a medical setting by a clinician for IUI treatments. IUI syringes are generally thinner and longer than ICI syringes in order to extend through the cervix for direct delivery of sperm into the uterus. ICI syringes are generally round at the distal end to block the cervical opening to prevent the released sperm from traveling backward into the vagina. ICI syringes can be difficult to handle by users who are not medical professionals, e.g. pushing the plunger in with one hand while lying down.

ICI kits occasionally include a sperm collection jar in addition to the fertility syringe. Unfortunately, the jars normally comprise traditional round containers with inside seams or cracks where sperm can become trapped, thus reducing the amount that can be transferred to the syringe.

Current sterilized syringes are often not designed for insemination, while at home insemination syringes are not sterilized. Research on the vaginal microbiome and diagnoses of infertility have becoming increasingly present in the art. This research demonstrates the need for sterilized at home syringes, designed for intracervical insemination within the art to reduce likelihood of introducing infection. (Xu et al., (2020) "Fertility factors affect the vaginal microbiome in women of reproductive age" *American J of Reproductive Immunology*, 83(4); Garcia-Velasco, J, et al. (2020) "The reproductive microbiome-clinical practice recommendations for fertility specialists", RBMO, 41(3): 443-453; Garcia-Velasco, J, et al. (2017) "What fertility specialists should know about the vaginal microbiome: a review", *RBM online*, page 103-112; and Gupta, S, et al. (2019) "Crosstalk between Vaginal Microbiome and Female Health: A review", *Microbial Pathogenesis*, 136(103696): 1-10).

What is needed in the art of at-home ICI treatments, is sterilized disposable fertility syringes and sperm collection jars for use by non-medical professionals to significantly reduce the costs of treatment while increasing the efficacy in delivering the maximum amount of sperm to the user's cervix. At a minimum, the fertility syringes should be easy to use with one-hand; the collection jars should be seamless inside; and the syringe structure should be able to deliver all of the sperm to the target site while leaving a minimum amount in the syringe.

SUMMARY OF THE INVENTION

Various embodiments of the present invention comprise a sterilized ICI fertility syringe, and a fertility kit for performing self-insemination, comprising a container with one to three sets of the disposable sterilized ICI fertility syringes individually wrapped and a sperm collection jar. Each fertility syringe comprises: an outer rigid tubular barrel and an inner plunger. The barrel comprises a curved distal end with a small circular distal opening, and a sealed proximal end, and an inner hollow tube housing the plunger. The barrel's proximal end also comprises two opposing circular members to fit a user's fingers; and a plunger flat end fitting in-between. The plunger distal end has a circular rubber with a tubular member that fits into the barrel curved end to push all the semen out while preventing a backflow. The collection jar comprises a sealable lid, and an inner surface comprising smooth seamless edges. Fresh semen is deposited into the jar, pulled into the syringe, and administered intra-cervically during a user's maximum monthly level of luteinizing hormone.

Various embodiments of the present invention further comprise an intracervical insemination (ICI) fertility kit for performing at home self-insemination, comprising at least one set (e.g. preferably three sets) of: a) a disposable, plastic sterile fertility syringe; and b) a sperm collection jar, which are shipped together in a package with instructions.

The sterile ICI fertility syringe comprises: a) an outer rigid tubular barrel comprising a curved distal end with a distal opening and a sealed proximal end, and said barrel enclosing an inner hollow tube with a narrowed distal opening joined to the barrel distal opening; b) the barrel sealed proximal end further comprising a handle combination comprising two opposing substantially hollow circular members able to fit a user's fingers; and c) a plunger positioned within the inner hollow tube and able to slide within to draw up and expel semen from the distal opening.

The plunger further comprises a distal end encircled by rubber seal positioned to tightly fit within (or flush to) the barrel curved distal end. And the plunger further comprises a tubular end distal to the rubber seal, said tubular end positioned to fit tightly within the tube narrowed distal opening to push all of the semen out of the distal opening. And the plunger further comprises a proximal end comprising a flat handle positioned to fit within the barrel circular members when the syringe is closed/retracted. And the plunger further comprises parallel ribs, divided into three sections of equal length, encircling and extending the length of the plunger.

The collection jar comprises a hand-held container and a sealable lid, and an inner surface comprising smooth seamless edges to prevent semen from being trapped within the seamless edges. It holds about 34 milliliter volume; and is round shaped on the outer and inner surface. In an embodiment, the sperm collection jars comprise a screw top or snap on lid. With a screw top, threads on the lid match threads on the container-jar.

The ICI fertility kit further comprises a transparent or opaque plastic wrapper sealing one or more of the fertility syringes to keep them sterile.

The ICI fertility kit further comprises a container or box or package for shipping the one or more sets, said package comprising a printed instructions on a method of using the fertility kit, and/or a printed website link or QR code to the instructions.

In an embodiment, the ICI fertility kit may further comprise an ovulation calendar to track luteinizing hormone result levels; and/or luteinizing test strips.

Various embodiments of the present invention further comprise a kit enclosing a plurality of individually packaged sterile fertility syringes and sperm collections jars, such as three sets thereof. If the kit comprises one set of syringe and collection jar, then a user will need three kits for a one-month treatment. If the kit comprises three sets of syringes and collection jars, then the user will only need one kit for one month of treatment.

In an embodiment, the sperm collection jars comprise a screw top or snap on lid; and round edges on the outer surface and inner walls. The later prevents the sperm from collecting in the jar's inner seams, thus making the majority of the sperm able to be extracted from the jar into the fertility syringe.

The present invention further comprises a method of use of the kit disclosed herein to complete a one-month round of at-home fertility treatments, comprising the steps of: 1) providing a fertility kit housing one-three sets of sterile fertility syringes and collection jars; 2) determining a user's calendar date of displaying a maximizing luteinizing hormone levels; 3) receiving a fresh deposit of a clean semen sample within the collection jar; 4) holding an unwrapped, sterile fertility syringe vertically in the collection jar, and withdrawing all of the semen sample into the fertility syringe by pulling upward on the plunger; 5) while lying down, inserting the sterility syringe until it is flush with a user's cervical opening, then pushing the plunger one or two-handedly inward to release all of the semen sample into the cervix; 6) remaining lying down for at least a half hour; and 7) repeat steps (1)-(6) two times per month with the two remaining sets of syringes and jars. The treatments are done in three consecutive days. The first application is the day before the user has reached their maximum luteinizing hormone level for the month. The second application should be done on the day of the users maximum luteinizing hormone level, and the third application the day after the luteinizing hormone peak.

One aspect of the present invention is to provide a fertility syringe that is able to reach the cervical opening to provide targeted delivery of the sperm directly to the cervical opening. This decreases the distance the sperm needs to 'swim' to meet the egg. This is especially helpful for anyone experiencing male factor infertility, such as decreased sperm motility or abnormal sperm morphology.

Another aspect is that the fertility syringes are sterilized, and then packaged in sterile, air-tight plastic wraps. Scientific studies have linked certain bacterial species present in the vaginal microbiome to women with unknown (or idiopathic) infertility. The sterilized syringes of the present invention bypass these bacteria if present. Sterilized syringes also decrease the introduction of new bacteria into the microbiome, which can impact fertility.

Another aspect is that the large opening of the syringe tip combined with the scientifically engineered plunger cap, works to minimize sperm sample waste so that the maximum amount of sperm is dispersed from the syringe leaving a minimal residual sperm within the syringe.

Another aspect is a novel syringe with an elongated and curved distal tip, with a circular opening to maximize a user's chances of impregnating by reaching to, and increasing the surface area contact with the user's cervix. The curved end allows insemination to occur directly at the cervical opening.

Another aspect is the structure of the plunger and barrel distal end to create a one-way like valve that prevents the sperm from remaining in the syringe when the plunger is completely pushed in. This is due to the plunger's funnel like end and pointed tip, pushing all sperm out of the barrel's hollow tube hole, which is aligned with the barrel outer hole. The plunger's pointed tip plugs these holes to prevent any backwash of the sperm.

Another aspect is the novel syringe's combination handle that allows the user to hold the syringe one-handedly, while pushing the plunger completely in. The user holds the syringe with their index and middle finger through the barrel circular loops, and pushes the plunger in with their thumb; and while lying on their back, preferably on a pillow or with their hips otherwise elevated.

Another aspect is the collection jars hold unwashed, fresh or frozen sperm.

The objects features and effects of the invention are described in detail below with accompanied drawings and embodiments. The aforementioned objects of the present invention are attained by an apparatus and method that functions for fertilization. Other objects, advantages and novel features of the present invention will become readily apparent from the following drawings and detailed description of preferred embodiments.

BRIEF DESCRIPTION OF THE DRAWINGS

The above and other features, aspects, and advantages of the present disclosure will become better understood with regard to the following description, appended claims, and accompanying drawing herein.

DETAILED DESCRIPTION OF EXEMPLARY EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

And although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As used herein, the term "assembly" and "unit" and "apparatus" may be used interchangeably.

As used herein, the term "proximal" refers to the end of the syringe closest to the user's hands and comprising the end where the user pushes the plunger in/out; and the term "distal" refers to the end of the syringe furthest from the user's hands, and where the semen is ejected from.

As used herein, the term "substantially" and "generally" refers to being significantly similar to the indicated shape or amount as recognized by one of ordinary skill in the art.

As used herein, the term "about" refers to plus or minus 10% of the recited value, e.g.; within +/−5%; within +/−2%; etc.

Figure 3A:
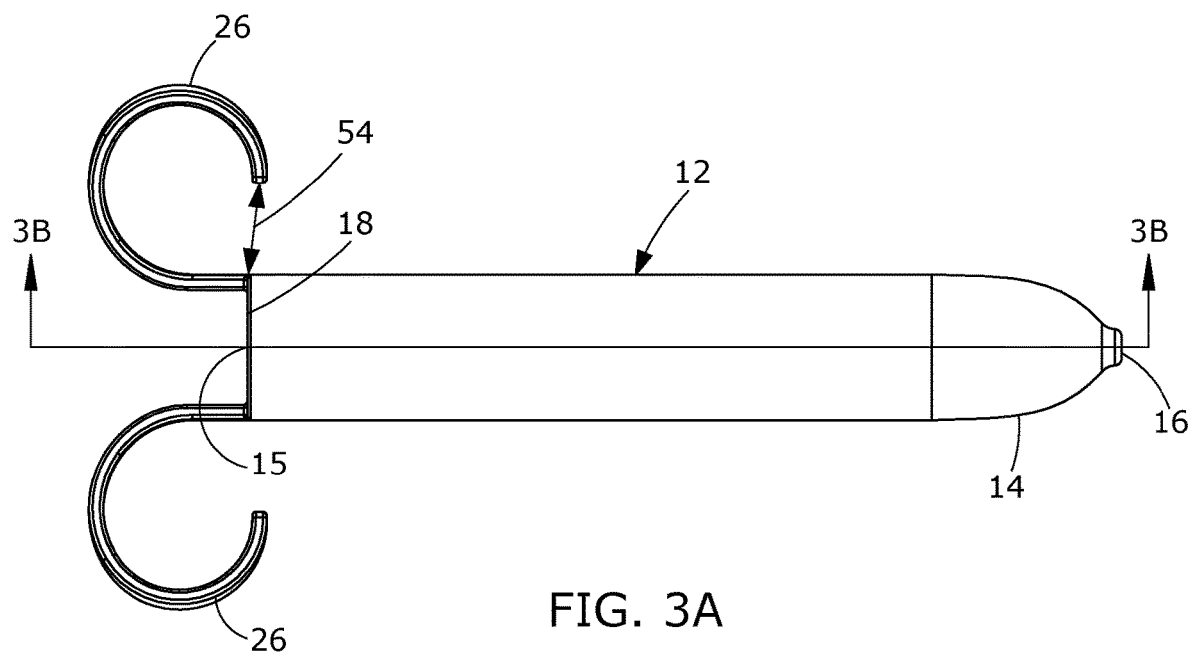
FIG. 3A is a side view of the outer surface of the barrel showing the curved handles for the index and middle finger.
Figure 3B:
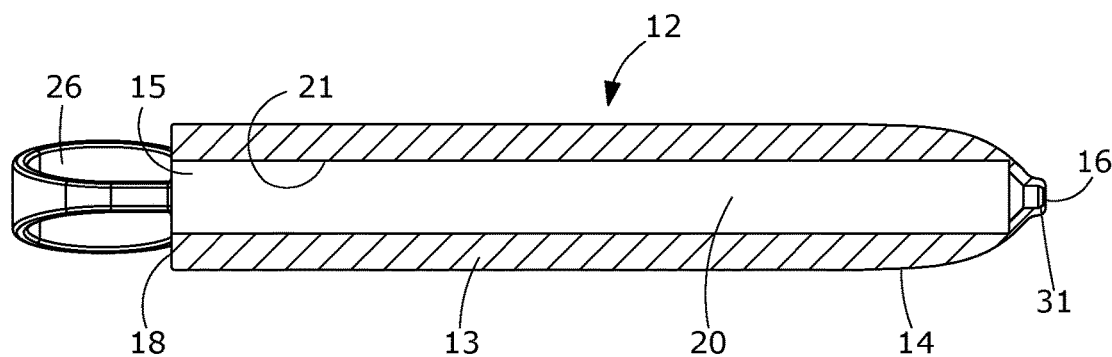
FIG. 3B is a cross-sectional view of an embodiment of the syringe showing the barrel is solid except for the inner hollow tube, which has a funnel-like distal end matching the plunger's distal end.
Figure 4A:
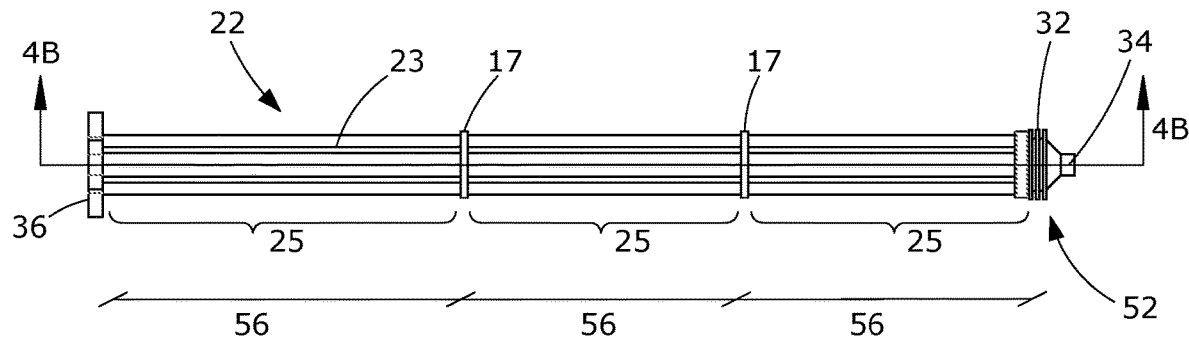
FIG. 4A is a side view of an embodiment of the plunger illustrating the parallel ribs and three sections.
Figure 4B:
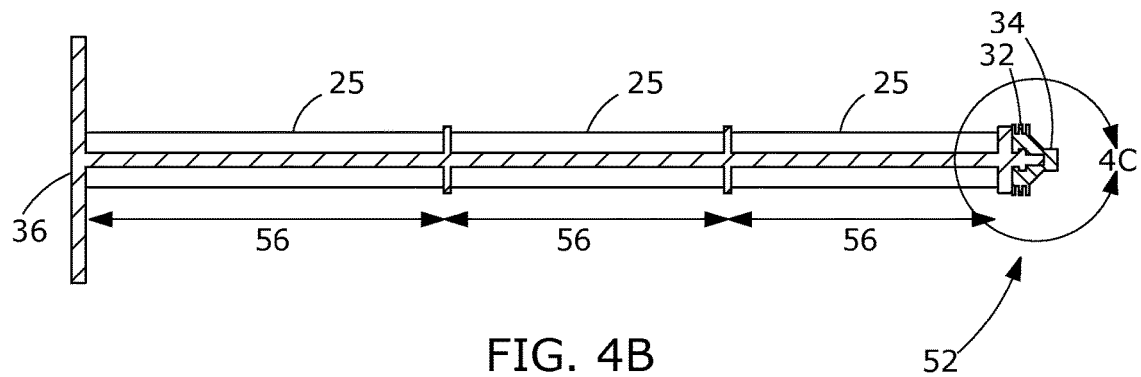
FIG. 4B is a cross-sectional view of the plunger taken along the length of FIG. 4A.
Figure 4C:
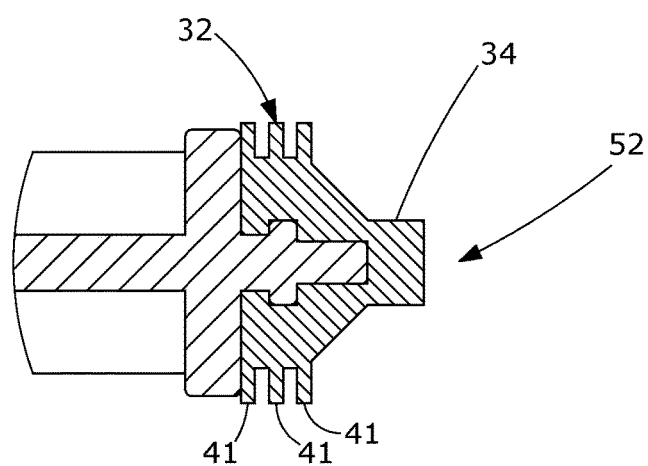
FIG. 4C is an exploded view of the distal end of the plunger rubber rings and extension that is funnel-like shaped to fit into and plug the distal end of the barrel (e.g. one-way valve).
Figure 4D:
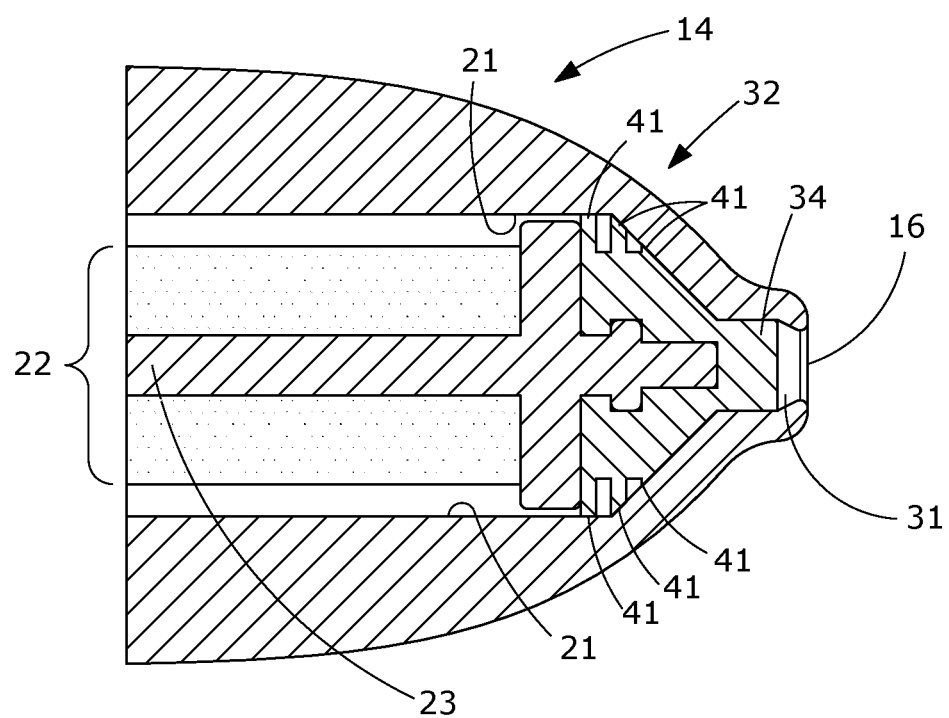
FIG. 4D is an exploded cross-sectional view of the plunger distal end of FIG. 4C.
Figure 5:
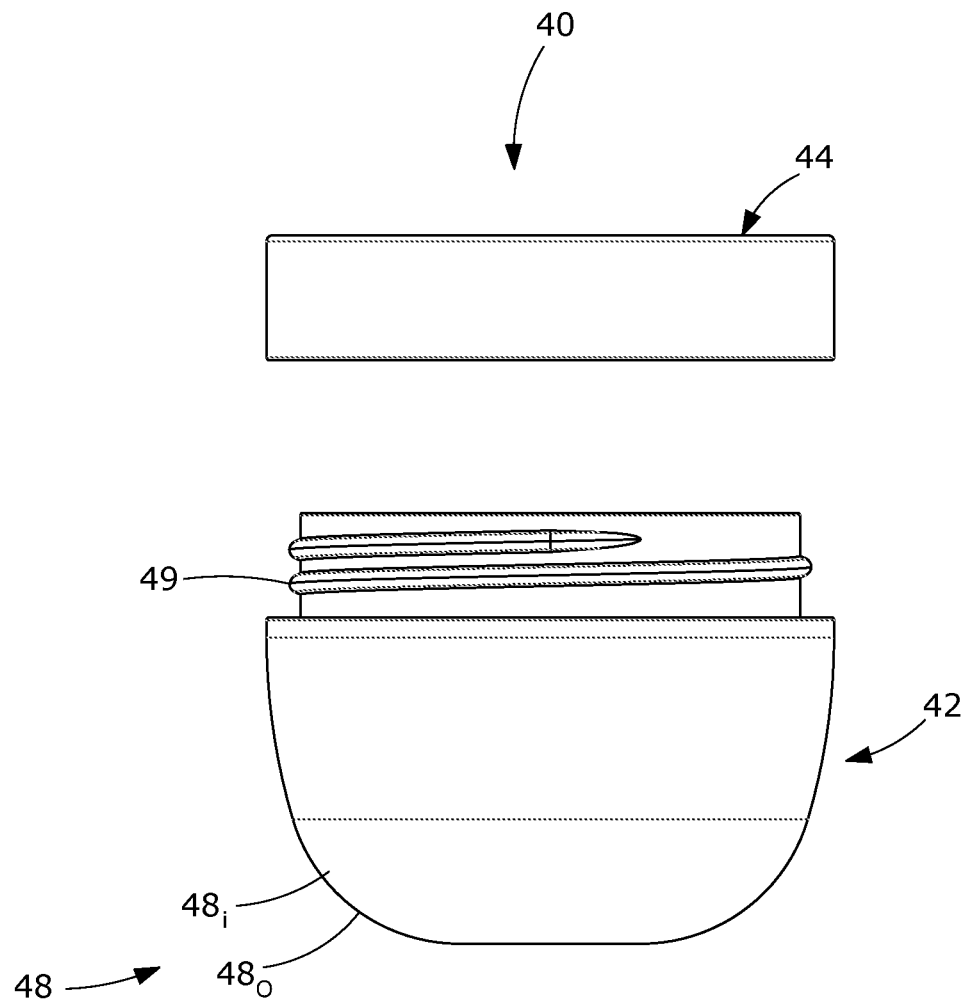
FIG. 5 is a view of an exemplary sperm collection jar used within the fertility kits of the present invention.
Figure 6:
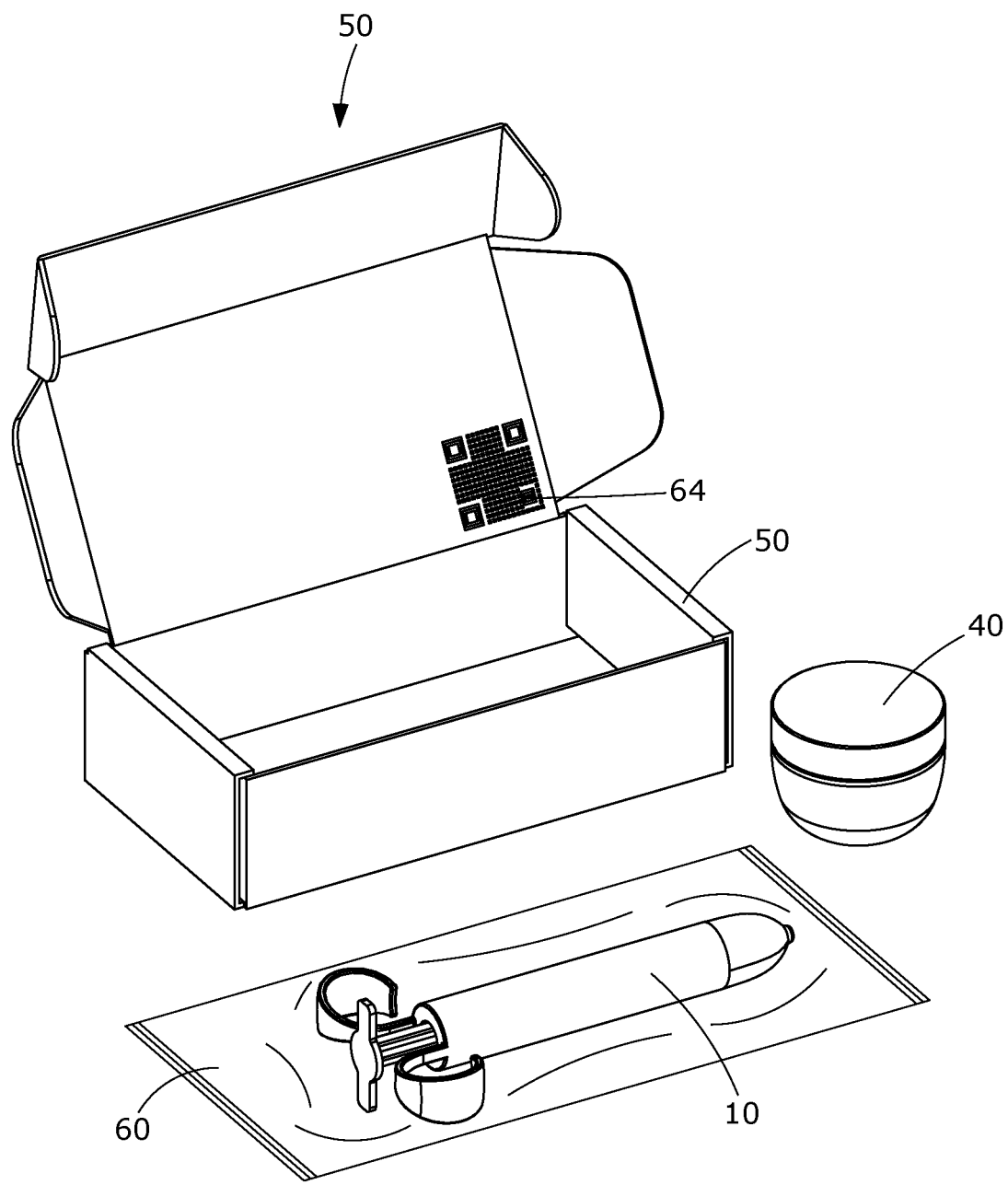
FIG. 6 is an illustration of a kit comprising plastic wrappers sealing the syringes to keep them sterile, and round collection jars without inner seams.

FIGS. 1-6 illustrate one exemplary embodiment of the fertility kits of the present invention: FIGS. 1-4C, syringe 10; FIG. 5 a sperm collection jar 40; and FIG. 6 a fertility kit 50.

Syringe

As illustrated in FIGS. 1-4C, each fertility syringe comprises a proximal end 35 and a distal end 30, and the general components of: an outer barrel 12 with a hollow tube 20 centered along the barrel length; and a plunger 22 that easily slides back and forth through tube 20.

The syringe also has a handle unit combining: circular members 26 attached to the barrel 12; and with a flat head end 36 attached to the plunger 22. This combination allows a user (if necessary), to hold and control the movement of the plunger using just three fingers: thumb, index, and middle finger. Preferably the user has both hands available to stabilize the syringe.

In an exemplary embodiment, syringe 10 is about 125-130 mm in length and about 72 mm in width due to the handle loops 26 (but about 20 mm at barrel 12).

Syringe Barrel

FIG. 3A is an illustration of an exemplary side view of the outer surface of barrel 12; and FIG. 3B is a longitudinal cross-section view of FIG. 3A, rotated ninety degrees. In an exemplary embodiment, the syringe's barrel comprises: an outer rigid tubular barrel 12, a center hollow tube 20, and a curved distal end 14 (e.g. generally half oval shaped and about 26 mm in length). This distal end further comprises a small circular distal opening 16 (e.g. about 2.4 to 3 mm in diameter).

As shown in the cross-sectional view of FIG. 3B, barrel 12 may be made of solid opaque material 13 (except for the hollow tunnel 20). In another embodiment, the space between barrel outer body 12 and tube 20 is hollow.

The middle of the barrel houses a hollow tube 20 with inner walls 21, and having a cross-sectional area of about 10 mm in diameter, while the entire barrel has a cross-sectional area of about 20 mm, in one exemplary embodiment.

Tube 20 distal end tapers inward to form a funnel-like shape that matches the distal end 52 of the plunger 32, 34 (see FIGS. 4A-4D). This funnel member either: 1) forms a small narrowed distal opening 31, which aligns and may be joined to the barrel distal opening 16; or 2) joins directly to distal opening 16. Either (1) or (2) allows semen to be pulled into and ejected from the hollow tube 20 while the plunger ends 32, 34 can plug barrel hole 16 to function as a one-way valve after the semen is ejected.

The barrel proximal end comprises a perpendicularly positioned disc 18 with a hole 15 equal to the plunger diameter, and forming a sealed proximal end that prevents plunger 22 from fully detaching from barrel 12. Proximal end 18 further comprises one part of the handle combination, two opposing loop members 26.

Plunger

FIG. 4A illustrates a side view of plunger 22; FIG. 4B is a longitudinal cross-sectional view thereof; and FIG. 4C is a magnified view of the plunger's distal end. Plunger 22 slides smoothly distally and proximally through the barrel hollow tube 20, while contacting the tube's inner walls 21 to push all the semen out of the distal opening 16. In an embodiment, the length of plunger 22 is about 135 to 137 mm, the diameter is about 9.5 mm, and the diameter of tube 20 is about 10 mm.

As illustrated in the close-up view of FIG. 4C and cross-sectional view 4D, plunger 22 further comprises on the distal end a circular rubber ring 32 (e.g., a plug), with or without individual rings 41 (e.g., 3 total); and may further comprise a tubular extension 34 (e.g., a pin or "pointed tip") adjoined distally to the rubber ring(s) 32. Ring 32 and pin 34 form a funnel-like shape and are sized to fit tightly into the both the barrel's hollow tube 20 distal end with opening 31 and the barrel's distal end opening 16 (e.g., see FIG. 3B). This enables the expulsion all of the semen from the syringe, while also functioning as a one-way valve (e.g., the opening 16 is too small and blocked by 32, 34 so as to prevent any semen from re-entering the syringe). In an embodiment, plunger 22 further comprises a plurality of parallel ribs 23

(e.g., 5 total) evenly spaced around the plunger, and extending its length (proximal to distal). Plunger 22 may also be divided into multiple sections 25 along its length, e.g., three sections of about equal length, with a flat disc 17 joining two aligned sections 25. Parallel ribs 23 and sections 25 facilitate plunger 22 to slide smoothly back and forth through tube 20 by minimizing the surface contact area, and by making the plunger more rigid.

Syringe Handles

As illustrated in FIGS. 1-3B, the syringe handle combination comprises: 1) the barrel's two looped rings 26; and 2) the plunger's flat end 36, which is rotated 90 degrees to fit in-between loops 26. Barrel loops comprise two opposing substantially hollow, circular members 26 able fit a user's index and middle fingers. In an embodiment, the inner diameter of circular members 26 is about 25 mm; and the circular members 26 do not form a complete circular, but rather about 75%. In another embodiment, they form a complete hollow circle.

Figure 1:
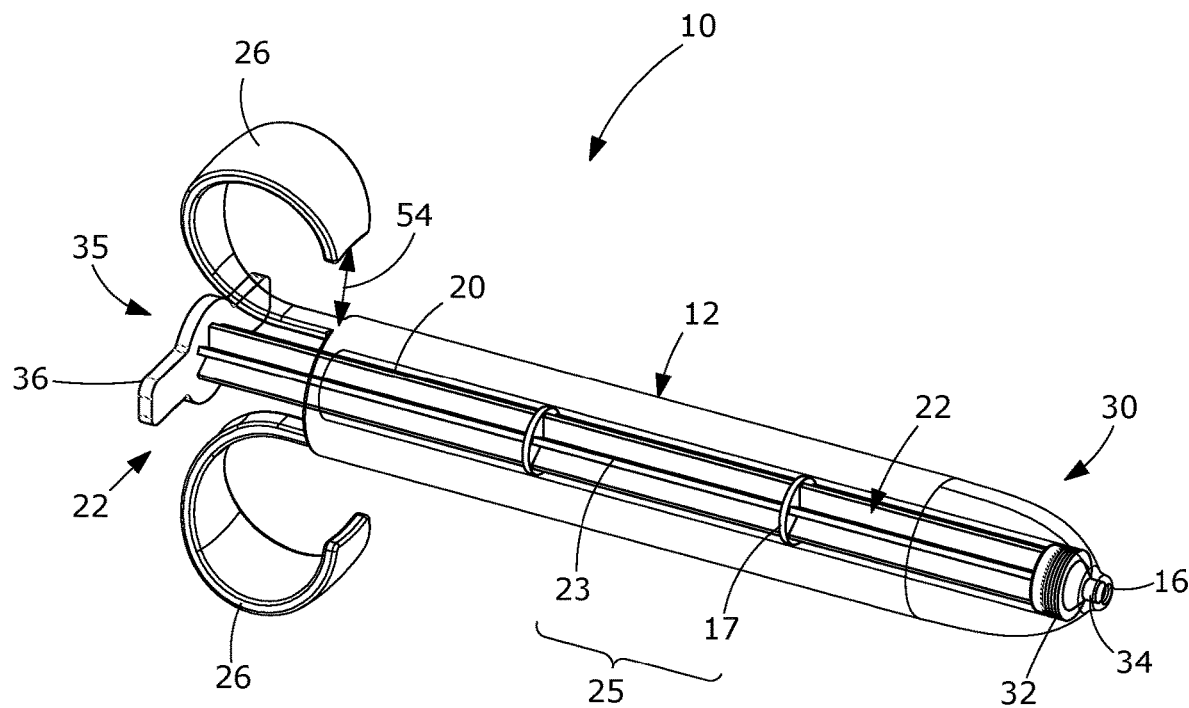
FIG. 1 is a perspective view of the fertility syringe in a closed position with the plunger fully inserted within the barrel.
Figure 2:
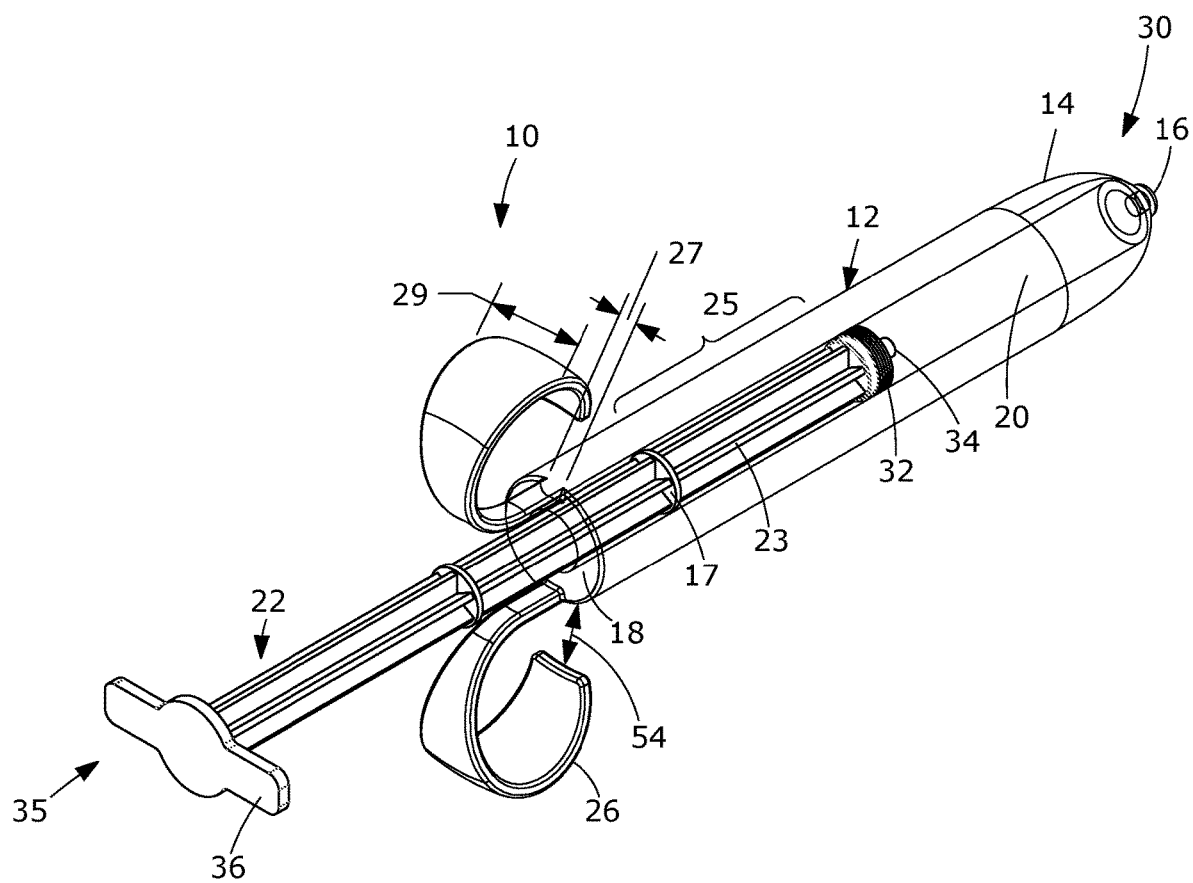
FIG. 2 is another perspective view of the fertility syringe with the plunger partially withdrawn from the barrel.

In an embodiment, the shape of circular members 26 also tapers wider while extending outward from barrel proximal end 18. As shown in FIG. 2, at end 18 the minimum width 27 of a circular member 26 is about 2-3 mm; and the maximum width 29 is about 15 to 16 mm. In another embodiment, circular members 26 have a uniform width the entire length. And plunger flat end 36 is rotated to fit in-between circular members 26 when the plunger is completely pushed in via a user's thumb on flat end 36. Plunger flat end 36 may also comprise a variety of substantially thin about 2 mm flat shapes, such as rectangular, or oval, or the exemplified, center circle with opposing rectangular ends.

Collection Jars

FIG. 5 is an illustration of an exemplary sperm collection jar 40 comprising a round hand-held container 42 and a sealable lid 44 with inner threads matching the container threads 49. Container 42 comprising round smooth seamless edges 48 on the outer surface 48o and on the inner surface 48i, the round smooth seamless edges 48 on the inner surface 48i prevent semen from being trapped within the seamless edges. In one embodiment, jar 40 can hold up to 30-34 milliliters volume, and it about 50 mm width on the lid. and about 40 mm height.

ICI Fertility Kits

In an exemplary embodiment, kits 50 of the present invention comprise: at least one set (e.g., three sets total) of sterile fertility syringes 10 and collection jars 40, which are shipped in one container (e.g., a substantially rectangular shaped, recyclable, cardboard box 50). For example, one kit comprises one treatment with one collection jar 40 and one packaged syringe 10. A user would buy three kits for one month of treatment. In another embodiment, three sets of collection jars and syringes come in the same package.

Each fertility syringe is individually packaged with a transparent or opaque plastic wrapper 60 to keep the syringe sterile. In another embodiment, two or three fertility syringes are sealed within one plastic wrapper 60.

The kits may further comprise printed instructions 62 and/or a website link or QR code 64 that is printed on the outside or inside of the shipping box. Instructions may further comprise a website link or QR code for downloading a calendar of the present invention for a user to track their ovulation cycle.

Method of Use of Kits

The method of use of kits 50 comprise the user first determining their ovulation cycle. This can be done using a calendar downloaded herein, and/or by using a third-party test kit or strips for measuring their luteinizing hormone level (e.g., a non-digital ovulation predictor kit—OPK). In another embodiment, the OPK or the like, is included in package 50.

Once a user determines when they are near their monthly maximum luteinizing hormone level, the sperm donor should deposit a fresh or recently thawed sperm sample into a clean sperm collection jar 40 and seal it closed.

The user then removes the lid 44, unwraps a sterile syringe 10, and positions the syringe vertically in collection jar 40. The user then pulls up on plunger 22 until all of the sperm is within the syringe. In an additional embodiment, the user may re-use the syringe while still lying down, so as to inject all of the semen remaining in the jar (e.g., two or more consecutive injections). The syringe is not laid down or touched in between injections.

Then while lying down and holding the syringe in their dominant hand using their index and middle fingers inserted into syringe loops 26, the user inserts the distal end of the syringe into their vagina until it is flush with their cervical opening. They then push the plunger handle 36 inward or distally with their thumb to release all of the semen sample into their cervical opening (e.g., plunger distal ends 32, 34 are against barrel hole 16 and the plunger cannot further move distally). After administering the sperm sample or specimen, the user should remain lying down for at least a half hour.

In an embodiment, each kit 50 comprises three sets of syringes 10 and collection jars 40; for use the day before, of, and after a user's maximum luteinizing hormone for that ovulation cycle. Hence, the user should administer a sperm sample during these three days (i.e. day before peak, day of peak, day after peak). If a pregnancy does not result, the user can repeat the process in a subsequent month. As with all forms of infertility treatment, it could take 3-6 months in order for the user to become pregnant with this method of ICI.

CONCLUSION

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A sterile An intracervical insemination (ICI) fertility kit for performing at home self-insemination, comprising:
   a) a disposable, sterilized plastic fertility syringe (10) comprising,
      i) an outer rigid tubular barrel (12), comprising a curved distal end (14) with a barrel distal opening (16) and a sealed proximal end (18), and said barrel enclosing an inner hollow tube (20) with a narrowed distal end at an opening (31) joined to the barrel distal opening (16);
      ii) the barrel sealed proximal end (18) further comprising a handle combination comprising two opposing substantially hollow circular members (26) with a small opening (54) near the outer rigid tubular barrel (12) and able to fit a user's fingers;

iii) a plunger (22) positioned within the inner hollow tube (20) and able to slide within said tube (20) to draw up and expel semen from the barrel distal opening (16);

wherein the plunger further comprises a plunger distal end (52) encircled by a rubber seal (32) comprising a plurality of flexible rings (41) positioned to tightly fit within the tube (20) to prevent semen backflow proximally;

wherein the plunger further comprises a tubular end (34) distal to the rubber seal (32), said tubular end positioned to fit tightly within the tube narrowed distal end at the opening (31) to push all of the semen out of the barrel distal opening (16);

wherein the plunger further comprises a proximal flat handle (36) rotated to fit between the barrel handle hollow circular members (26) when the plunger is completely pushed into the barrel; and b) a collection jar (40) comprising a hand-held container (42) and a sealable screw top or snap on lid (44), and comprising round shaped smooth seamless edges (48) on an inner surface (48i) and outer surface (48O) of the hand-held container, the seamless edges of the inner surface prevent the semen from being trapped within the seamless edges.

2. The ICI fertility kit of claim 1, wherein the plunger (22) further comprises a plurality of parallel ribs (23), divided into three sections (25) of about equal length (56), encircling and extending a length of the plunger.

3. The ICI fertility kit of claim 1, wherein the snap on lid holds about 30-34 milliliters.

4. The ICI fertility kit of claim 3, wherein the semen is unwashed, and fresh or frozen.

5. The ICI fertility kit of claim 1, further comprising a substantially flat transparent or opaque plastic wrapper (60) sealing the fertility syringe to keep the fertility syringe sterile.

6. The ICI fertility kit of claim 1, further comprising a container (50) for shipping the fertility kit, said container comprising printed instructions on a method of using the fertility kit, and a printed website link or a QR code to said instructions.

7. The ICI fertility kit of claim 1, wherein the distal end of both the inner tube (20) and the plunger (34) are funnel-like shaped and the funnel-like shape of the plunger is sized to fit tightly into the inner tube and matches the funnel-like shape of the inner tube to prevent semen backflow proximally and to eject all of the semen from the fertility syringe.

8. A method of using an intracervical insemination (ICI) fertility kit for performing at home self-insemination, comprising the steps of:

1) providing a fertility kit housing one or more sets of:
   a) a disposable, sterilized plastic fertility syringe (10) comprising,
      i) an outer rigid tubular barrel (12), comprising a curved distal end (14) with a barrel distal opening (16) and a sealed proximal end (18), and said barrel enclosing an inner hollow tube (20) with a narrowed distal end at an opening (31) joined to the barrel distal opening (16);
      ii) the barrel sealed proximal end (18) further comprising a handle combination comprising two opposing substantially hollow circular members (26) with a small opening (54) near the outer rigid tubular barrel (12) and able to fit a user's fingers;
      iii) a plunger (22) positioned within the inner hollow tube (20) and able to slide within said tube (20) to draw up and expel semen from the barrel distal opening (16);
      wherein the plunger further comprises a distal end (52) encircled by a rubber seal (32) comprising a plurality of flexible rings (41) positioned to tightly fit within the tube (20) to prevent semen backflow proximally;
      wherein the plunger further comprises a tubular end (34) distal to the rubber seal (32), said tubular end positioned to fit tightly within the tube narrowed distal end at the opening (31) to push all of the semen out of the barrel distal opening (16);
      wherein the plunger further comprises a proximal flat handle (36) rotated to fit between the barrel handle hollow circular members (26) when the plunger is completely pushed into the barrel; and
   b) a collection jar (40) comprising a hand-held container (42) and a sealable screw top or snap on lid (44), and comprising round shaped smooth seamless edges (48) on an inner surface (48i) and outer surface (48O) of the hand-held container, the seamless edges of the inner surface prevent the semen from being trapped within the seamless edges;

2) determining a user's calendar date of displaying a maximizing luteinizing hormone level;

3) Receiving a fresh deposit of a clean semen sample within the collection jar;

4) holding the fertility syringe vertically in the collection jar, and withdrawing all of the semen sample into the fertility syringe by pulling upward on the plunger;

5) while lying down, inserting the fertility syringe until it is flush with a user's cervix, then pushing the plunger distally to release all of the semen sample into the cervix;

6) after the plunger has been pushed distally, remaining lying down for at least a half hour; and 7) repeating steps (1)-(6) two more times; for a total of three injections occurring: a day before, a day of, and a day after a user's maximum luteinizing hormone level.

9. The method of using the ICI fertility kit of claim 8, wherein the plunger (22) further comprises parallel ribs (23), divided into three sections (25) of about equal length (56), encircling and extending a length of the plunger.

10. The method of using the ICI fertility kit of claim 8, wherein the snap on lid holds about 30-34 milliliters.

11. The method of using the ICI fertility kit of claim 10, wherein the semen sample is unwashed, and fresh or frozen.

12. The method of using the ICI fertility kit of claim 8, further comprising a substantially flat transparent or opaque plastic wrapper (60) sealing one or more of the fertility syringes to keep the one or more fertility syringes sterile.

13. The method of using the ICI fertility kit of claim 8, further comprising a container (50) for shipping the one or more sets, said container comprising printed instructions on the method of using the fertility kit, and a printed website link or a QR code to said instructions.

14. The method of using the ICI fertility kit of claim 8, wherein the distal end of both the inner tube (20) and the plunger (34) are funnel-like shaped and the funnel-like shape of the plunger is sized to fit tightly into the inner tube and matches the funnel-like shape of the inner tube to prevent semen backflow proximally and to eject all of the semen from the fertility syringe.

\* \* \* \* \*